United States Patent [19]

Speck et al.

[11] 4,181,721

[45] Jan. 1, 1980

[54] DEPOT PREPARATIONS IN AN OILY, UNSATURATED SOLUTION FOR INTRAMUSCULAR INJECTION

[75] Inventors: Ulrich Speck; Erwig Pinter; Ursula Lachnit-Fixson; Johann-Diederich Hahn-Godeffroy, all of Berlin, Fed. Rep. of Germany

[73] Assignee: Schering Aktiengesellschaft, Berlin, Fed. Rep. of Germany

[21] Appl. No.: 922,475

[22] Filed: Jul. 7, 1978

Related U.S. Application Data

[63] Continuation of Ser. No. 735,397, Oct. 26, 1976, abandoned.

[30] Foreign Application Priority Data

Oct. 27, 1975 [DE] Fed. Rep. of Germany ....... 2548413

[51] Int. Cl.² ............................................. A61K 31/56

[52] U.S. Cl. ............................ 424/243; 424/DIG. 14
[58] Field of Search ......................................... 424/243

[56] References Cited

U.S. PATENT DOCUMENTS

| 3,514,514 | 5/1970 | Lehmann et al. | 424/238 |
| 3,703,534 | 11/1972 | Casadio et al. | 424/243 |

*Primary Examiner*—Dale R. Ore
*Attorney, Agent, or Firm*—Millen & White

[57] ABSTRACT

In order to prolong the effectiveness of depot preparations of progestagens in an oily, unsaturated solution for intramuscular injection having long-term effectiveness sufficient for a desired purpose, the volume of the injection solution is increased such that the duration of the progestational activity is increased to at least 13 weeks while retaining the same quantity of active agent to be administered.

36 Claims, No Drawings

DEPOT PREPARATIONS IN AN OILY, UNSATURATED SOLUTION FOR INTRAMUSCULAR INJECTION

This is a continuation of application Ser. No. 735,397 filed Oct. 26, 1976, now abandoned.

BACKGROUND OF THE INVENTION

This invention relates to depot preparations in an oily, unsaturated solution suitable for intramuscular injection.

Injectable depot preparations are conventional. They exhibit the advantage over orally administered preparations that a single injection is sufficient for one or several months whereas tablets, for example, must generally be ingested daily. A depot effect is frequently produced by combining the active agent with a carrier substance which gradually releases the active agent. An additional depot effect can be achieved by using a derivative of the active agent which is degraded to the active agent only within the body.

Depot preparations of progestational substances are utilized, for example, as contraceptives. For example, an oily solution of 17α-ethynyl-19-nortestosterone enanthate is a depot contraceptive which has been clinically tested for years. With a dose of 200 mg. in 1 ml. of castor oil/benzyl benzoate (6:4), the depot effect lasts about 12 weeks. However, it has been found that the number of pregnancies is somewhat larger than in case of a daily, oral tablet administration since undesired pregnancies occur, especially shortly before the expiration of the injection interval. Besides, it would be desirable to obtain an effect which lasts over 13 weeks (3 months), because the administration intervals could then be calculated more readily, based on the menstrual cycle.

OBJECTS OF THE INVENTION

Accordingly, it is a general object of the present invention to provide sustained release pharmaceutical compositions suitable for intramuscular application which achieve an extended period of effectiveness without any increase in the amount of active medicinal agent employed.

Another object of the present invention is to provide such compositions which extend anti-contraceptive activity to three months or more, thereby extending the usefulness thereof to three complete menstrual cycles.

A further object of the present invention is to provide such preparations which permit quarterly administration of anti-contraceptive depot preparations on a calendar year basis.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing, in the intramuscular injection into a living mammal of a depot preparation comprising a pharmaceutically active amount of a lipophilic steroid having progestational activity dissolved in an oily, unsaturated carrier to achieve and maintain progestational activity for a desired period of time of at least several weeks, the improvement which comprises injecting a depot preparation consisting essentially of 50–500 mg. of a lipophilic steroid hormone having a progestational depot effect dissolved in 1–6 ml. of a mixture of castor oil/benzyl benzoate in a volume ratio of 6:4, whereby the time during which said progestational activity is maintained is increased to at least 13 weeks in comparison with a similar dosage level of said hormone in a lesser amount of said carrier.

DETAILED DISCUSSION

It has now been found that a prolongation of the depot effect occurs if the volume of the injection solution is increased while retaining the amount of active agent to be administered.

Female beagles weighing about 13 kg. were injected simultaneously into the right and left M. gluteus with 200 mg. of 14,15-$^3$H-tagged norethisterone enanthate and 4-$^{14}$C-tagged norethisterone enanthate, respectively, in 1.8 ml. and in 0.6 ml. of castor oil/benzyl benzoate (6:4). For 13 weeks, the $^{14}$C and $^3$H activity was determined in the blood, plasma, urine, and feces. The excretion of the tagged compounds, proportional to their release from the depot preparation, shows no systematic difference between the selected volumes of application until up to 7 weeks after administration. Only a very minor reduction of the release from the larger volume, with the initially high release rates, can be observed. Starting with the eighth week, the proportions of the tag applied to the larger volume predominate. In the 13th week after administration, the release from the injection volumes in favor of the 1.8 ml. solution has increased by three and a half times, i.e. in the 13th week a release was observed which was about 3.5 times higher than with the smaller volume.

The measured values for the 13th week are indicated in the following column-type diagram.

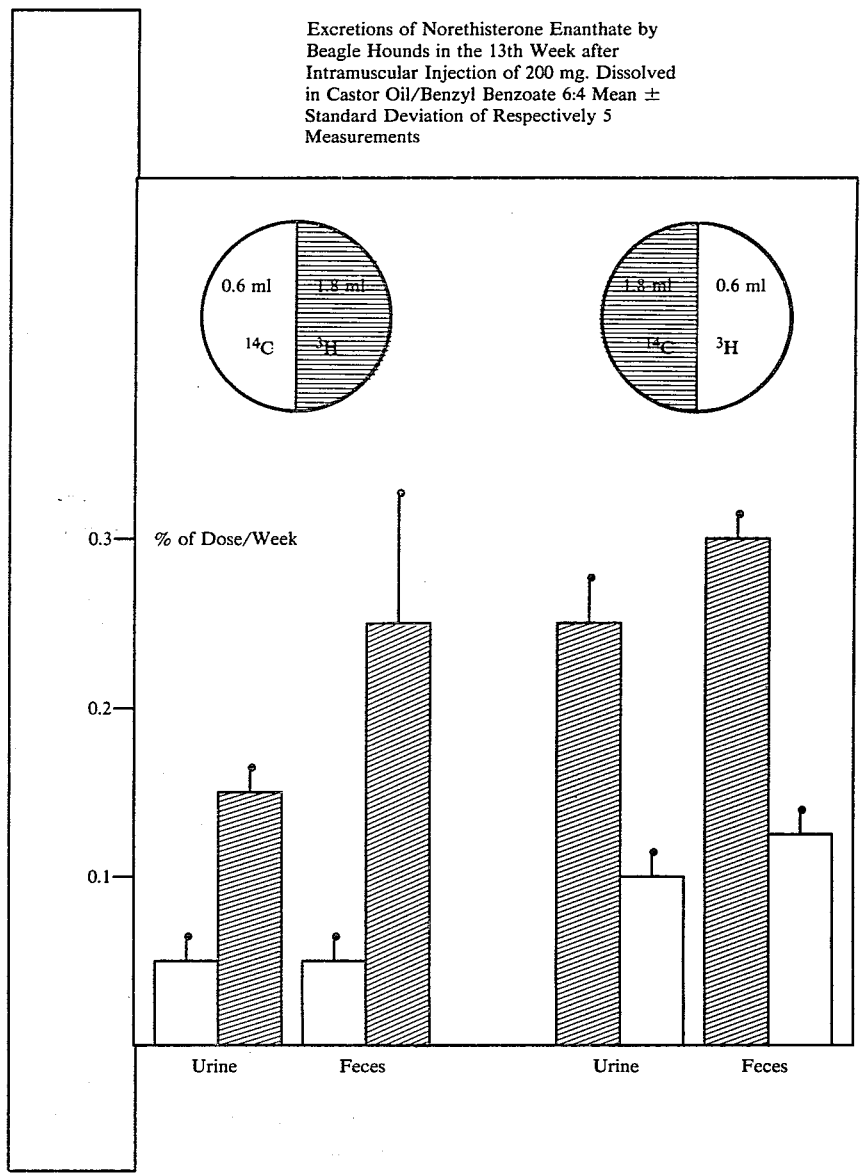

Excretions of Norethisterone Enanthate by Beagle Hounds in the 13th Week after Intramuscular Injection of 200 mg. Dissolved in Castor Oil/Benzyl Benzoate 6:4 Mean ± Standard Deviation of Respectively 5 Measurements It could not be foreseen that, with the identical quantity of active agent, a protracted release of active agent and thus a prolongation of the duration of effectiveness after intramuscular injection takes place by increasing the volume of the solution.

Due to the prolonged duration of effectiveness obtained by increasing the injection volume, 200 mg. of norethisterone enanthate is now sufficient for safe and reliable protection against conception over a period of three months for women of childbearing age. Smaller or larger amounts of active agent, respectively, are required for a shorter or longer period than 3 months. In general, 50–500 mg., preferably 200–400 mg., of norethisterone enanthate, or corresponding amounts of an analogous depot progestogen, are utilized in 1–6 ml., preferably 2–4 ml. of an oily solution.

The prolongation of the duration of effectiveness occurs even with only a minor increase in volume; however, it is advantageous to raise the solvent volume by one and one-half to three times. An enlargement of the solvent volume beyond such value is in principle possible in accordance with this invention, but is not recommended since volumes of such a size, when administered intramuscularly, often lead to complaints.

Accordingly, this invention relates to depot preparations in an oily, unsaturated solution for intramuscular injection, with a long-lasting effect sufficient for the desired purpose, characterized by increasing the volume of the injection solution in order to prolong effectiveness, while retaining the conventional quantity of active agent to be administered.

The depot preparations of the present invention comprise an oily, unsaturated solution for intramuscular injection with a long-lasting effectiveness sufficient for the desired purpose, and are prepared by dissolving one or more lipophilic active agents in an oily solvent or mixtures thereof, diluting the saturated solution to one and one-half to three times the volume of the saturated solution, filtering the solution under sterile conditions, dispensing the solution in the usual manner into ampoules of 1, 2, 3 or 4 ml. and sterilizing the ampoules.

Preferred active medicinal agents are compounds which, due to their chemical structure, already display a protracted effectiveness and wherein a long-term treatment is indicated on account of their spectrum of activity. Such compounds are known in the art and include but are not limited to lipophilic steroid hormones, especially steroid alcohols in the form of their physiologically hydrolyzable esters. Preferably suitable are steroids having a progestational, estrogenic or androgenic activity, for example, for fertility control in humans and animals or for the treatment of climacteric complaints in women. Combinations of, for example, progestational and estrogenic, or estrogenic and androgenic active are also possible.

Examples of progestational steroid hormones are the esters of 17-hydroxyprogesterone and of 19-nor-17-hydroxyprogesterone; 17-hydroxyprogesterone derivatives, e.g., the 17-esters of 6α-methyl-17-hydroxyprogesterone, 6-methyl-6-dehydro-17-hydroxyprogesterone, 6-chloro- or 6-fluoro-6-dehydro-17-hydroxyprogesterone, 6-chloro- or 6-fluoro-6-dehydro-16α-methyl-17-hydroxyprogesterone, 6,16α-dimethyl-6-dehydro-17-hydroxyprogesterone, 1α,2α-methylene-6-chloro- or -6-fluoro-6-dehydro-17-hydroxyprogesterone; esters of 17α-ethynyl-19-nortestosterone, 17α-ethynyl-18-methyl-19-nortestosterone, 17α-ethynyl-4-estrene-3,17β-diol, 17α-ethynyl-4-estren-17β-ol, etc.

Especially suitable as estrogens are the esters of estradiol, estriol; estrone and ethynylestradiol. As androgenic compounds, particularly suitable are the esters of testosterone, 1α-methylandrostan-17β-ol-3-one and dehydroepiandrosterone.

The esters are derived from physiologically compatible acids. Preferred are the esters of organic carboxylic acids of 4–20, preferably 4–12, carbon atoms. The acids can be aliphatic, cycloaliphatic, aromatic, aromatic-aliphatic or heterocyclic, and are well known in the art. These acids can also be unsaturated and/or polybasic and/or substituted in the usual manner, e.g., by alkyl, hydroxy, alkoxy, oxo or amino groups, or by halogen atoms.

The following esters are presently preferred: butyrates, valerates, caproates, enanthates, pelargonates, undecylates, benzoates, β-cyclopentylpropionates, phenylacetates, etc.

A 3-keto group present in the steroid hormone can be functionally modified and can be present, for example, as an enol ester or enol ether group. In case of an enol ester group, the above-mentioned ester residues are suitable, as well as acetates and propionates. In case of an enol ether group, the ether residue can be a preferably lower alkyl residue, e.g., methyl or ethyl. Also suitable are cyclic alkyl residues, e.g., cyclopentyl or cyclohexyl.

The effective dosage is dependent on the purpose of the treatment, the type of active agent and the desired duration of effectiveness. This dosage is, for example, in case of 17α-ethynyl-19-nortestosterone enanthate for fertility control in the human female for 3 months, 200 mg. In place of 17α-ethynyl-19-nortestosterone enanthate, comparable depot progestogens can also be employed. The amount of comparable progestogens administered is equal to that corresponding to the application of 200 mg. of 17α-ethynyl-19-nortestosterone enanthate for three months.

The preparations are injected intramuscularly in an oily solution. The injection volume according to this invention is 1–6 ml. The active agents are dissolved in an oily solvent suitable for injection, as known to those skilled in the art for such purposes, in 1.5 to 3 times the customarily required quantity of solvent, filtered under sterile conditions and aseptically filled into ampoules.

Examples for oily solvents are sesame oil and castor oil. In order to raise the solubility of the active agent, solubilizers can be added to the oily solvent, e.g., benzyl benzoate or benzyl alcohol. In addition to the aforementioned oils, it is also possible to employ other vegetable oils, e.g. linseed oil, cottonseed oil, sunflower oil, peanut oil, olive oil, wheat-germ oil and similar oils. Also suitable are synthetic oils, such as polyethylene glycol, triglycerides of higher saturated fatty acids, monoesters of higher fatty acids, etc. A mixture of castor oil/benzyl benzoate in a ratio of 6:4 is preferred as the solvent.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

2000 mg. of 19-nor-17α-ethynyltestosterone enanthate is dissolved in a mixture of castor oil/benzyl benzoate (6:4) and the solution is then filled up to 20 ml. The sterile-filtered solution is then dispensed into 2 ml. ampoules in the usual manner under aseptic conditions. The ampoules are finally sterilized for 2 hours at 120° C.

EXAMPLE 2

2000 mg. of 19-nor-17α-ethynyltestosterone enanthate is dissolved in a mixture of castor oil/benzyl benzoate (6:4) and the solution is then filled up to 30 ml. The sterile-filtered solution is dispensed into ampoules of 3 ml. in the usual manner under aseptic conditions. The ampoules are finally sterilized for 2 hours at 120° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In the intramuscular injection into a living mammal of a depot preparation comprising a progestationally effective amount of a lipophilic, physiologically hydrolyzable 17α-ethynyl-19-nortestosterone carboxylic acid ester having progestational activity dissolved in an oily, unsaturated carrier which is a mixture of castor oil and benzyl benzoate which imparts a depot effect to the progestational activity for a desired period of time of at least several weeks, the improvement wherein the amount of said steroid ester is 50–500 mg and the amount of carrier is increased to 1–6 ml whereby said increased amount of carrier extends the progestational activity of the ester to at least 13 weeks.

2. The process of claim 1, wherein the amount of said steroid ester is 200–400 mg and the amount of said carrier is increased to 2–4 ml.

3. The process of claim 2, wherein said ester is 17α-ethynyl-19-nortestosterone enanthate.

4. The process of claim 2, wherein the volume ratio of castor oil to benzoyl benzoate is 6:4.

5. The process of claim 3, wherein the volume ratio of castor oil to benzyl benzoate is 6:4.

6. In a depot preparation adapted for intramuscular injection into a living mammal and comprising a progestationally effective active amount per unit dosage of a lipophilic, physiologically hydrolyzable 17α-ethynyl-19-nortestosterone carboxylic acid ester having progestational activity dissolved in an oily, unsaturated carrier which is a mixture of castor oil and benzyl benzoate which imparts a depot effect to the progestational activity for a period of time of at least several weeks, the improvement wherein the amount of said steroid ester is 50–500 mg and the amount of carrier is increased to 1–6 ml whereby said increased amount of carrier extends the progestational activity of the ester to at least 13 weeks.

7. The depot preparation of claim 6 wherein the amount of said steroid ester is 200–400 mg and the amount of said carrier is increased to 2–4 ml.

8. The process of claim 7, wherein said ester is 17α-ethynyl-19-nortestosterone enanthate.

9. The process of claim 7, wherein the volume ratio of castor oil to benzyl benzoate is 6:4.

10. The process of claim 8, wherein the volume ratio of castor oil to benzyl benzoate is 6:4.

11. A method of increasing to at least 13 weeks the duration of progestational activity of 50–500 mg of a lipophilic, physiologically hydrolyzable 17α-ethynyl-19-nortestosterone carboxylic acid ester having progestational activity dissolved in an oily, unsaturated carrier which is a mixture of castor oil and benzyl benzoate which imparts a depot effect to the progestational activity for a desired period of time of at least several weeks, which comprises increasing the amount of carrier to 1–6 ml without increasing the amount of steroid ester whereby said increased amount of carrier extends the progestational activity of the ester to at least 13 weeks.

12. The method of claim 11 wherein the amount of said steroid ester is 200–400 mg and the amount of said carrier is increased to 2–4 ml.

13. The process of claim 12, wherein said ester is 17α-ethynyl-19-nortestosterone enanthate.

14. The process of claim 12, wherein the volume ratio of castor oil to benzyl benzoate is 6:4.

15. The process of claim 13, wherein the volume ratio of castor oil to benzyl benzoate is 6:4.

16. The process of claim 5, wherein 200 mg of the steroid ester are dissolved in 2–3 ml of the carrier.

17. The depot preparation of claim 10, wherein 200 mg of the steroid ester are dissolved in 2–3 ml of the carrier.

18. The method of claim 15, wherein 200 mg of the steroid ester are dissolved in 2–3 ml of the carrier.

19. The process of claim 5, wherein 200 mg of the steroid ester are dissolved in 2 ml of the carrier.

20. The depot preparation of claim 10, wherein 200 mg of the steroid ester are dissolved in 2 ml of the carrier.

21. The method of claim 15, wherein 200 mg of the steroid ester are dissolved in 2 ml of the carrier.

22. The process of claim 2, wherein 200 mg of the steroid ester are dissolved in 2 ml of the carrier.

23. The depot preparation of claim 7, wherein 200 mg of the steroid ester are dissolved in 2 ml of the carrier.

24. The method of claim 12, wherein 200 mg of the steroid ester are dissolved in 2 ml of the carrier.

25. The process of claim 1, wherein the amount of said steroid ester is 50–400 mg and the amount of said carrier is increased to 1–4 ml.

26. The process of claim 1, wherein the amount of said steroid ester is 50–200 mg and the amount of said carrier is increased to 1–2 ml.

27. The process of claim 1, wherein the amount of said steroid ester is 200–500 mg and the amount of said carrier is increased to 2–6 ml.

28. The process of claim 1, wherein the amount of said steroid ester is 400–500 mg and the amount of said carrier is increased to 4–6 ml.

29. The depot preparation of claim 6, wherein the amount of said steroid ester is 50–400 mg and the amount of said carrier is increased to 1– ml.

30. The depot preparation of claim 6, wherein the amount of said steroid ester is 50–200 mg and the amount of said carrier is increased to 1–2 ml.

31. The depot preparation of claim 6, wherein the amount of said steroid ester is 200–500 mg and the amount of said carrier is increased to 2–6 ml.

32. The depot preparation of claim 6, wherein the amount of said steroid ester is 400–500 mg and the amount of said carrier is increased to 4–6 ml.

33. The method of claim 11, wherein the amount of said steroid ester is 50–400 mg and the amount of said carrier is increased to 1–4 ml.

34. The method of claim 11, wherein the amount of said steroid ester is 50–200 mg and the amount of said carrier is increased to 1–2 ml.

35. The method of claim 11, wherein the amount of said steroid ester is 200–500 mg and the amount of said carrier is increased to 2–6 ml.

36. The method of claim 11, wherein the amount of said steroid ester is 400–500 mg and the amount of said carrier is increased to 4–6 ml.

* * * * *